(12) United States Patent
Wiggers

(10) Patent No.: US 11,179,215 B2
(45) Date of Patent: Nov. 23, 2021

(54) ROBOTIC ARM CART WITH FINE POSITION ADJUSTMENT FEATURES AND USES THEREFOR

(71) Applicant: Verb Surgical Inc., Mountain View, CA (US)

(72) Inventor: Robert T. Wiggers, Belmont, CA (US)

(73) Assignee: VERB SURGICAL INC., Santa Clara, CA (US)

( * ) Notice: Subject to any disclaimer, the term of this patent is extended or adjusted under 35 U.S.C. 154(b) by 0 days.

(21) Appl. No.: 16/653,565

(22) Filed: Oct. 15, 2019

(65) Prior Publication Data

US 2020/0038130 A1    Feb. 6, 2020

Related U.S. Application Data

(62) Division of application No. 15/725,093, filed on Oct. 4, 2017, now Pat. No. 10,485,623.

(60) Provisional application No. 62/513,798, filed on Jun. 1, 2017.

(51) Int. Cl.
*F16M 11/00* (2006.01)
*A61B 50/13* (2016.01)
*A61B 34/30* (2016.01)
*B25J 9/00* (2006.01)
(Continued)

(52) U.S. Cl.
CPC .............. *A61B 50/13* (2016.02); *A61B 34/30* (2016.02); *A61B 90/57* (2016.02); *B25J 9/0009* (2013.01); *A61B 2017/00477* (2013.01); *A61B 2090/571* (2016.02)

(58) Field of Classification Search
CPC ......... A61B 90/57; A61B 34/30; A61B 50/13; B25J 9/0009
See application file for complete search history.

(56) References Cited

U.S. PATENT DOCUMENTS

| 5,351,676 A | 10/1994 | Putnam |
| 5,876,325 A | 3/1999 | Mizuno et al. |
| 5,878,193 A | 3/1999 | Wang et al. |

(Continued)

FOREIGN PATENT DOCUMENTS

| CN | 103448643 | 12/2013 |
| CN | 105213030 | 1/2016 |

(Continued)

OTHER PUBLICATIONS

Notice of Reasons for Rejection for Japanese Application No. 2019-563141 dated Oct. 27, 2020, 6 pages.

(Continued)

*Primary Examiner* — Amy J. Sterling
(74) *Attorney, Agent, or Firm* — Womble Bond Dickinson (US) LLP

(57) ABSTRACT

Some embodiments described herein relate to an arm cart operable to transport a robotic arm to and/or from a surgical table. The robotic arm can be coupled to the arm cart via a connector. The connector can be slideably mounted to the arm cart such that the connector and the robotic arm, collectively, can move relative to the arm cart. For example, when the arm cart is adjacent to the surgical table, the connector and the robotic arm can be movable to provide final, fine adjustments to align the robotic arm with a coupling portion of the surgical table.

14 Claims, 8 Drawing Sheets

(51) Int. Cl.
  *A61B 90/57* (2016.01)
  *A61B 17/00* (2006.01)

(56) References Cited

U.S. PATENT DOCUMENTS

| | | | |
|---|---|---|---|
| 6,330,890 | B1 | 12/2001 | Ekman |
| 8,496,647 | B2 * | 7/2013 | Blumenkranz ........ A61B 34/37 606/1 |
| 9,694,839 | B2 | 7/2017 | Canady et al. |
| 10,034,721 | B1 | 7/2018 | Timm et al. |
| 10,333,296 | B1 | 6/2019 | Wu et al. |
| 2006/0161136 | A1 | 7/2006 | Anderson et al. |
| 2010/0012798 | A1 | 1/2010 | Blum et al. |
| 2010/0243344 | A1 | 9/2010 | Wyrobek et al. |
| 2013/0085389 | A1 | 4/2013 | Tsang et al. |
| 2014/0297130 | A1 | 10/2014 | Griffiths et al. |
| 2015/0190201 | A1 | 7/2015 | Olson |
| 2017/0065354 | A1 | 3/2017 | Shiels et al. |
| 2017/0065355 | A1 | 3/2017 | Ross et al. |
| 2017/0079730 | A1 | 3/2017 | Azizian et al. |
| 2017/0135771 | A1 | 5/2017 | Auld et al. |
| 2018/0078439 | A1 | 3/2018 | Cagle et al. |
| 2018/0147106 | A1 | 5/2018 | Soundararajan et al. |
| 2018/0207794 | A1 | 7/2018 | Sebring et al. |
| 2018/0271604 | A1 | 9/2018 | Grout et al. |
| 2018/0333215 | A1 | 11/2018 | Timm et al. |
| 2018/0344421 | A1 | 12/2018 | Cagle et al. |
| 2018/0361568 | A1 | 12/2018 | Cagle et al. |
| 2018/0362060 | A1 | 12/2018 | Schaller et al. |
| 2020/0000536 | A1 * | 1/2020 | Yakimovich ............. B25J 19/06 |

FOREIGN PATENT DOCUMENTS

| | | |
|---|---|---|
| CN | 105310775 | 2/2016 |
| EP | 0752237 | 1/1997 |
| EP | 2145586 | 1/2010 |
| EP | 2893898 | 7/2015 |
| GN | 110868954 | 3/2020 |
| JP | H02059468 | 5/1990 |
| JP | H04019729 | 2/1992 |
| JP | H06297378 | 10/1994 |
| JP | H08224243 | 9/1996 |
| JP | 2000-255428 | 9/2000 |
| JP | 2007276063 | 10/2007 |
| JP | 2014158942 | 9/2014 |
| JP | 2017513550 | 6/2017 |
| KR | 10-2010-0067846 | 6/2010 |
| KR | 10-2016-0135240 | 11/2016 |
| WO | 2015142798 | 9/2015 |
| WO | 2015175203 | 11/2015 |
| WO | 2016048738 | 3/2016 |
| WO | 2016054256 | 4/2016 |
| WO | 2016069661 | 5/2016 |
| WO | 2017083453 | 5/2017 |
| WO | 2017085094 | 5/2017 |
| WO | 2018053282 | 3/2018 |
| WO | 2018217518 | 11/2018 |
| WO | 2018222470 | 12/2018 |

OTHER PUBLICATIONS

Extended European Search Report for European Application No. 18808974.2 dated Nov. 23, 2020, 9 pages.
Notice of Reasons for Rejection for Japanese Application No. 2019-563192 dated Nov. 4, 2020, 7 pages.
Notice of Acceptance for Australian Application No. 2018278218 dated Nov. 10, 2020, 4 pages.
Notice of Reasons for Rejection for Japanese Application No. 2019-563190 dated Oct. 27, 2020, 6 pages.
Examination Report for Australian Application No. 2018341716 dated Oct. 12, 2020, 3 pages.
Extended European Search Report for European Application No. 18806664.1 dated Nov. 19, 2020, 7 pages.
Examiner's Report for Canadian Application No. 3,060,359 dated Dec. 17, 2020, 3 pages.
Examiner's Report for Canadian Application No. 3,060,993 dated Dec. 18, 2020, 4 pages.
Extended European Search Report for European Application No. 18810600.9 dated Dec. 11, 2020, 7 pages.
Extended European Search Report for European Application No. 18820247.7 dated Dec. 14, 2020, 7 pages.
Examiner's Report for Canadian Application No. 3,060,879 dated Dec. 17, 2020, 4 pages.
Notice of Reasons for Rejection for Japanese Application No. 2019-563290 dated Dec. 8, 2020, 7 pages.
Examination Report for Australian Application No. 2018278218 dated Jul. 13, 2020, 4 pages.
International Preliminary Report on Patentability for International Application No. PCT/US2018/033056, dated Dec. 5, 2019, 6 pages.
International Preliminary Report on Patentability for International Application No. PCT/US2018/034229, dated Dec. 12, 2019, 6 pages.
International Preliminary Report on Patentability for International Application No. PCT/US2018/034945, dated Dec. 12, 2019, 6 pages.
International Preliminary Report on Patentability for International Application No. PCT/US2018/036566, dated Jan. 2, 2020, 6 pages.
Australian Examination Report for Australian Application No. 2018276946 dated Jan. 24, 2020, 4 pages.
International Preliminary Report on Patentability for International Application No. PCT/US2018/035900, dated Apr. 9, 2020, 6 pages.
Australian Examination Report for Australian Application No. 2018271773 dated Jan. 31, 2020, 4 pages.
Notice of Office Action for Korean Application No. 10-2019-7034862 dated Feb. 22, 2021, 6 pages.
Examiner's Decision of Refusal for Japanese Application No. 2019-563192 dated Mar. 30, 2021, 5 pages.
Examiner's Report for Canadian Application No. 3,060,997 dated Mar. 10, 2021, 3 pages.
Extended European Search Report for European Application No. 18862162.7 dated Mar. 18, 2021, 22 pages.
Examiner's Report for Canadian Application No. 3,074,438 dated Apr. 19, 2021, 5 pages.
Notice of Office Action for Korean Application No. 10-2019-7034549 dated Apr. 22, 2021, 16 pages.
Office Action and Search Report for Chinese Application No. 2018800409518 dated Apr. 8, 2021, 13 pages.
Notice of Office Action for Korean Application No. 10-2019-7037287 dated May 27, 2021, 15 pages.
Examination Report for Australian Application No. 2018289123 dated May 11, 2020, 4 pages.
Notice of Allowance for U.S. Appl. No. 15/785,331 dated Jul. 15, 2020, 16 pages.
Notice of Allowance for U.S. Appl. No. 15/785,341 dated May 26, 2020, 8 pages.
Notice of Office Action for Korean Application No. 10-2019-7033930 dated Jun. 9, 2021, 13 pages.
Notification of Reasons for Refusal for Japanese Application No. 2019-563290 dated Jun. 29, 2021, 8 pages.
Examiner's Decision of Refusal for Japanese Application No. 2019-563141 dated Jun. 29, 2021, 6 pages.
Examiner's Report for Canadian Application No. 3,060,359 dated Aug. 17, 2021, 4 pages.
Examiner's Decision for Refusal for Japanese Application No. 2019-563190 dated Jun. 22, 2021, 6 pages.
Examination Report for Australian Application No. 2020260428 dated Jul. 23, 2021, 8 pages.

* cited by examiner

ROBOTIC ARM CART WITH FINE POSITION ADJUSTMENT FEATURES AND USES THEREFOR

CROSS-REFERENCE TO RELATED APPLICATIONS

This application is a divisional of pending U.S. application Ser. No. 15/725,093, filed Oct. 4, 2017, which claims priority to U.S. Patent Application Ser. No. 62/513,798, filed on Jun. 1, 2017, which is hereby incorporated by reference in its entirety.

BACKGROUND

Embodiments described herein relate to apparatus and methods for a robotic arm cart for transporting, delivering, and securing robotic arms to, for example, a surgical table.

SUMMARY

Some embodiments described herein relate to an arm cart operable to transport a robotic arm to and/or from a surgical table. The robotic arm can be coupled to the arm cart via a connector. The connector can be slideably mounted to the arm cart such that the connector and the robotic arm, collectively, can move relative to the arm cart. For example, when the arm cart is adjacent to the surgical table, the connector and the robotic arm can be movable to provide final, fine adjustments to align the robotic arm with a coupling portion of the surgical table.

DETAILED DESCRIPTION

Figure 1A:
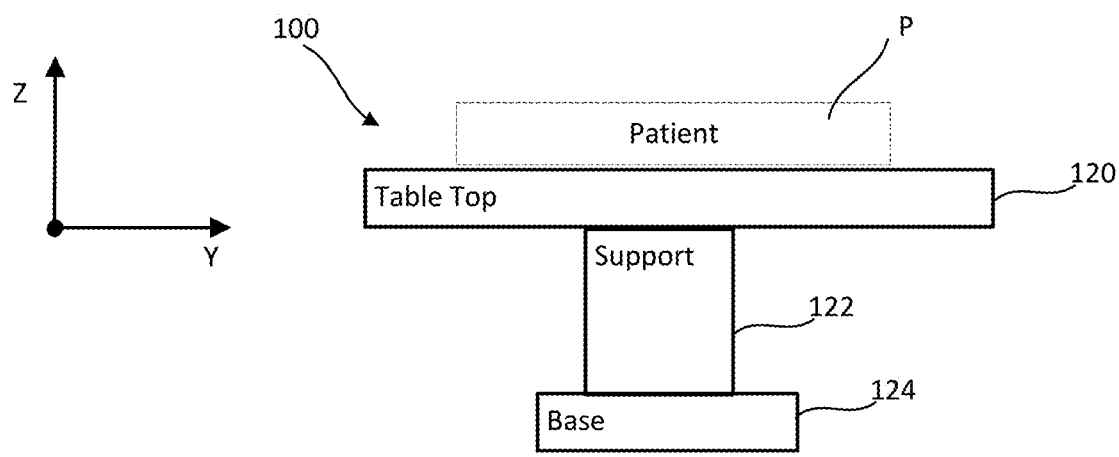
FIGS. 1A and 1B are a schematic side view and a schematic top view, respectively, of a surgical table, according to an embodiment.

Apparatus and methods for providing an arm cart for transporting, delivering, and securing robotic arms to a surgical table having a table top on which a patient can be disposed are described herein. When a robotic arm is delivered to the surgical table, in some instances, the robotic arm may not be precisely aligned with the surgical table. Some embodiments described herein relate to methods and apparatus suitable adjust the robotic arm within the arm cart, which can allow fine adjustments to the surgical arm such that the robotic arm can be more closely aligned to the surgical table.

A surgical table and a robotic arm can be configured to matingly couple. For example, the surgical table and the robotic arm can include complementary coupling portions, such as link and socket mating portions. An arm cart operable to support and/or transport the robotic arm may be suitable to move the robotic arm such that the coupling portion of the robotic arm is approximately aligned with the corresponding coupling portion of the surgical table. Challenges may exist, however, in precisely aligning the arm cart with the surgical table such that the robotic arm can mate with the surgical table. For example, it may be difficult for an operator to steer an arm cart exactly into a precise horizontal position. Moreover, floor coverings, manufacturing tolerances, and the like may result in the robotic arm not precisely aligning with the surgical table. Some embodiments described herein relate to an arm cart having a connector configured to support the robotic arm. The connector can be slideably mounted to the arm cart such that a position of the robotic arm can be adjusted relative to the arm cart. In this way, fine adjustments can be made to the position of the robotic arm, without moving/adjusting the entire arm cart. Fine adjustments can facilitate mating the robotic arm to the surgical table.

Some embodiments described herein relate to a method that includes moving an arm cart containing a robotic arm from a storage location to a surgical table. The arm cart can support the robotic arm in a first position in which a coupling portion of the robotic arm can be approximately aligned with a corresponding coupling portion of the surgical table. Similarly stated, in some embodiments, when the arm cart is moved into proximity with the surgical table, a mating portion of the robotic arm can be within 10-20 mm of a corresponding mating portion of the surgical table. In other embodiments, when the arm cart is moved into proximity with the surgical table, the robotic arm can be within 10 cm, 2 cm, or any other suitable distance of a corresponding mating portion of the surgical table. The robotic arm can be moved within and/or while still coupled to the arm cart from the first position to a second position, in which the coupling portion of the robotic arm is exactly aligned with the coupling portion of the surgical table. After the robotic arm is exactly aligned with the surgical table, the robotic arm can be coupled to the surgical table and/or decoupled from the arm cart.

Figure 1B:
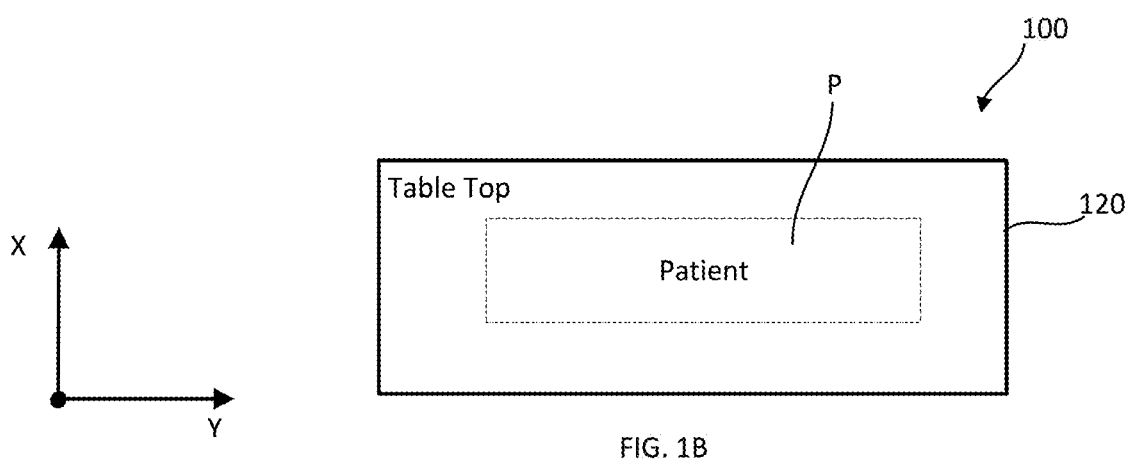

As shown schematically in FIGS. 1A-1B, a surgical table 100 includes a table top 120, a table support 122 and a table base 124. The table top 120 has an upper surface on which a patient P can be disposed during a surgical procedure, as shown schematically in FIG. 1A. The table top 120 is disposed on the support 122, which can be, for example, a pedestal, at a suitable height above the floor. The support 122 (also referred to herein as a pedestal) may provide for movement of the table top 120 in a desired number of degrees of freedom, such as translation in the vertical, or Z axis (height above the floor), horizontal Y axis (along the longitudinal axis of the table), and/or horizontal X axis (along the lateral axis of the table), and/or rotation about the Z, Y, and/or X axes. The table top 120 may also include multiple sections that are movable relative to each other along/about any suitable axes, e.g., separate sections for each of the torso, one or both legs, and/or one or both arms, and a head support section. Movement of the table top 120 and/or its constituent sections may be performed manually, driven by motors, controlled remotely, or through any other suitable means. The support 122 for the table top 120 may be mounted to the base 124, which can be fixed to the floor of the operating room, or can be movable relative to the floor, e.g., by use of wheels on the base 124. In some embodiments, the height of the support 122 can be adjusted, which together with, for example, the motion (e.g., axial (longitudinal) or lateral motion) of the table top 120, can allow for the table top 120 to be positioned at a desired surgical site at a certain height above the floor (e.g., to allow surgeon access) and a certain distance from the support 120. This also can allow robotic arms (e.g., arms 130 discussed below) coupled to the table 100 to reach a desired treatment target on a patient P disposed on the table top 120.

In a robotically-assisted surgical procedure, one or more robotic arms 130 (shown schematically in FIGS. 1C and 1D) can be disposed in a desired operative position relative to a patient disposed on the table top 120 of the surgical table 100 (also referred to herein as "table"). The robotic arm(s) can be used to perform a surgical procedure on a patient disposed on the surgical table 100. In particular, the distal end of each robotic arm can be disposed in a desired operative position so that a medical instrument coupled to the distal end of the robotic arm can perform a desired function.

Figure 1C:
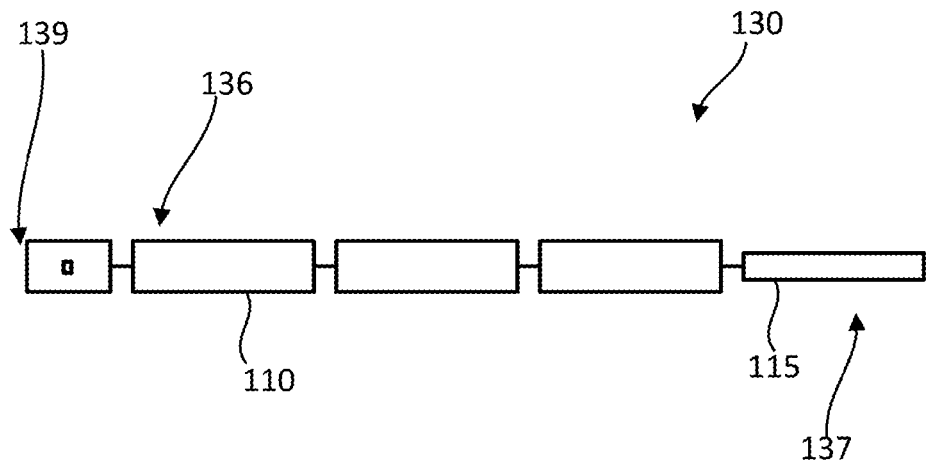
FIG. 1C is a schematic side view of a robotic arm, according to an embodiment, shown in an extended or use configuration.
Figure 1D:
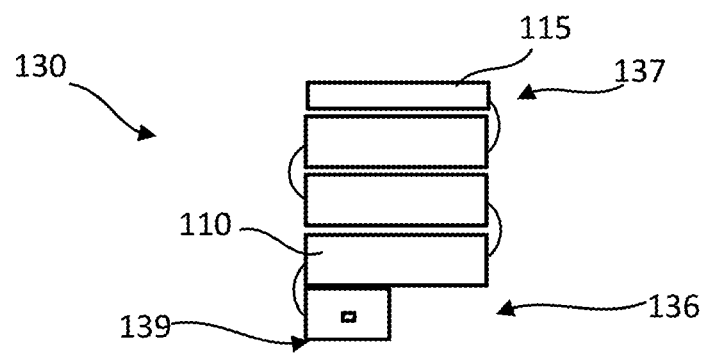
FIG. 1D is a schematic side view of the robotic arm of FIG. 1C, shown in a collapsed or folded configuration.

As shown schematically in FIGS. 1C and 1D, each robotic arm 130 can include a distal end portion 137 and a proximal end portion 136. The distal end portion 137 (also referred to herein as "operating end") can include or have coupled thereto a medical instrument or tool 115. The proximal end portion 136 (also referred to herein as the "mounting end portion" or "mounting end") can include the coupling portion to allow the robotic arm 130 to be coupled to the table 100. The robotic arm 130 can include two or more link members or segments 110 coupled together at joints that can provide for translation along and/or rotation about one or more of the X, Y and/or Z axes (shown, for example, in FIGS. 1A and 1B). The coupling portion of the robotic arm 130 can include a coupling mechanism 139. The coupling mechanism 139 can be disposed at the mounting end 136 of the arm 130 and may be coupled to a segment 110 or incorporated within a segment 110. The robotic arm 130 can be moved between various extended configurations for use during a surgical procedure, as shown in FIG. 1C, and various folded or collapsed configurations for storage when not in use, as shown in FIG. 1D.

Figure 2A:
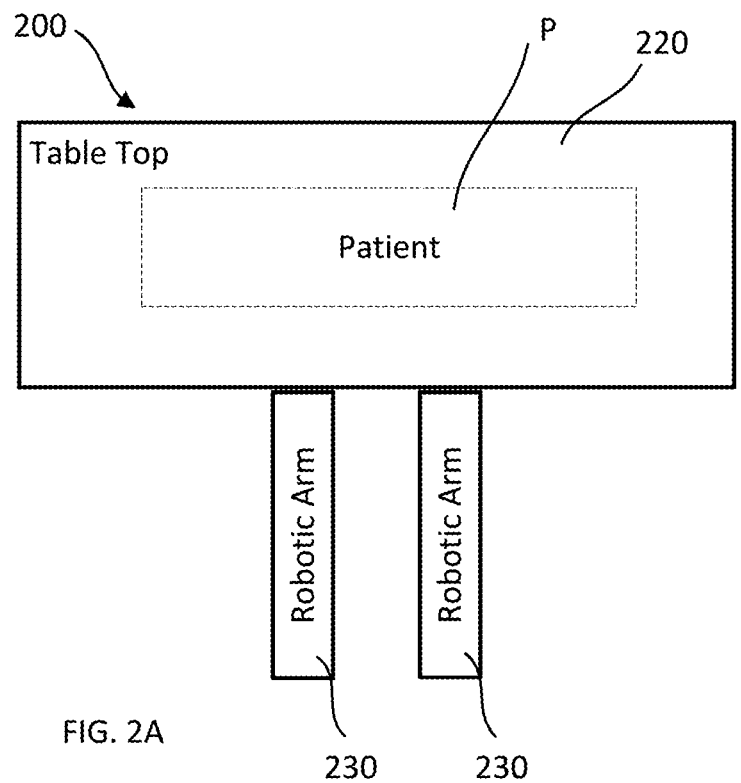
FIG. 2A is a schematic top view of a surgical table with robotic arms coupled thereto, according to an embodiment.
Figure 2B:
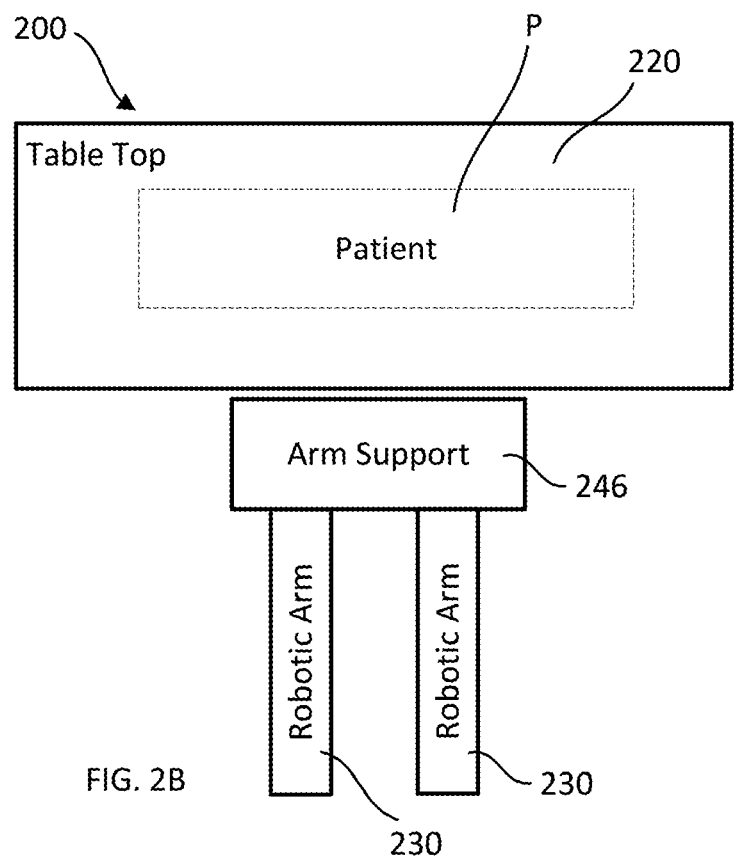
FIG. 2B is a schematic top view of a surgical table with robotic arms and an arm adapter coupled thereto, according to an embodiment.

FIGS. 2A and 2B illustrate two embodiments of a surgical table with a robotic arm coupled thereto. As described above and in accordance with various embodiments disclosed in more detail below, the robotic arm may be suitable for use in performing a surgical procedure and may be releasably coupled to a surgical table. In some embodiments, robotic arms can be coupled at a fixed location on the table or can be coupled such that the robotic arms can be movable to multiple locations relative to the table top. For example, as shown schematically in FIG. 2A, robotic arms 230 can be coupled to a table top 220 of a surgical table 200. The surgical table 200 can be the same or similar in structure and function to the surgical table 100 described above. For example, the table top 220 has an upper surface on which a patient P can be disposed during a surgical procedure. As shown schematically in FIG. 2B, in some embodiments, the robotic arms 230 can be coupled, in a fixed or movable location, to an arm adapter 246 that is coupled to or separate from the surgical table. The arm adapter 246 can be coupled to or separate from but engageable with or coupleable to the table top 220.

In preparation for a robotically-assisted surgical procedure in which one or more robotic arms are releasably coupled to the surgical table and/or to an arm adapter, as described with respect to FIGS. 2A and 2B, each robotic arm may be delivered and connected to the surgical table and/or the arm adapter via an arm cart. As shown schematically in FIG. 3, an arm cart 350 can be configured to support one or more robotic arms. The arm cart 350 includes a first robotic arm 330A and can include an optional second robotic arm 330B. Although two robotic arms 330 are shown, the arm cart 350 can be configured to contain, transport, and/or deliver any suitable number of robotic arms 330, such as, for example, one robotic arm, three robotic arms, or four robotic arms.

The arm cart 350 can be configured for movement. For example a base 354 of the arm cart 350 can include wheels. In some embodiments, the arm cart 350 can be configured to move the robotic arm 330 between one or more positions and/or one or more orientations, including, for example, between a storage location and a surgical location. A surgical location (e.g., an operating room) can include a surgical table 300. In this way, the robotic arm 330 can be brought into proximity (e.g., in contact with and/or within less than a 30 cm) of the surgical table 300. As described in further detail herein, the robotic arm 330 can then be coupled to the surgical table 300.

The surgical table 300 can include a table top 320, a table support 322, and a table base 324. The table top 320 has an upper surface on which a patient P can be disposed during a surgical procedure. The table top 320 is disposed on the support 322, which can be, for example, a pedestal, at a suitable height above the floor. The support 322 can be mounted to the base 324, which can be fixed to the floor of the operating room or can be moveable relative to the floor, e.g., by use of wheels on the base 324.

The surgical table 300 includes a coupling portion 346 configured to receive, be coupled to, and/or mate with a robotic arm (e.g., the robotic arm 330). In some embodiments, the coupling portion 346 can be coupled to or separate from but engageable with or coupleable to the table top 320 (e.g., the coupling portion 346 can be a portion of an adapter as shown and described with reference to FIG. 2B). In other embodiments, the coupling portion 346 can be integral with the table top 320 and/or the pedestal 322.

The arm cart 350 can support the first robotic arm 330A (and the optional second robotic arm 330B) in a variety of configurations. In some embodiments, the first robotic arm 330A can be coupled to the arm cart 350 via a connector 336. In embodiments in which the arm cart 350 contains (or is configured to contain) multiple robotic arms, the arm cart 350 can include multiple connectors 336 and/or each robotic arm can be connected and/or disconnected from one connector. In some embodiments, the connector 336 can be the sole support for the robotic arm 330 and, as described in further detail herein can be configured to move within the arm cart 350. In this way, the connector 336 can couple the robotic arm 330 to the arm cart 350, and the connector 336 and the robotic arm 350 can be operable to move within the arm cart 350, for example to allow for fine adjustments of the position of the robotic arm 330.

The robotic arm 330 includes a coupling portion 339, which, as described in further detail below, is configured to connect to and/or mate with the coupling portion 346 of the surgical table 300. In some embodiments, moving the arm cart 350 adjacent to the surgical table 300 can be suitable to move the coupling portion 339 of the robotic arm 330 near the coupling portion 346 of the surgical table. The coupling portion 339 of the robotic arm 330 can be approximately aligned with (e.g., vertically and/or laterally within 2 cm or any other suitable distance) of the coupling portion 346 of the surgical table 300. In some instances, however, moving the arm cart 350 and/or the surgical table 300 may provide only gross or approximate alignment. Similarly stated, in some instances, moving the arm cart 350 and/or the surgical table 300 may be insufficient to precisely align the coupling portion 339 of the robotic arm 330 with the coupling portion 346 of the surgical table such that the robotic arm 330 can be matingly coupled to the surgical table 300.

As described in further detail herein, the robotic arm 330 can be coupled to the arm cart 350 via the connector 336. The connector 336 can permit the robotic arm 330 to move within the arm cart 330 such that fine adjustments to the alignment of the coupling portion 339 of the robotic arm 330 can be made (e.g., to bring the coupling portion 339 of the robotic arm 330 into alignment with the coupling portion of the surgical table 300).

Figure 3:
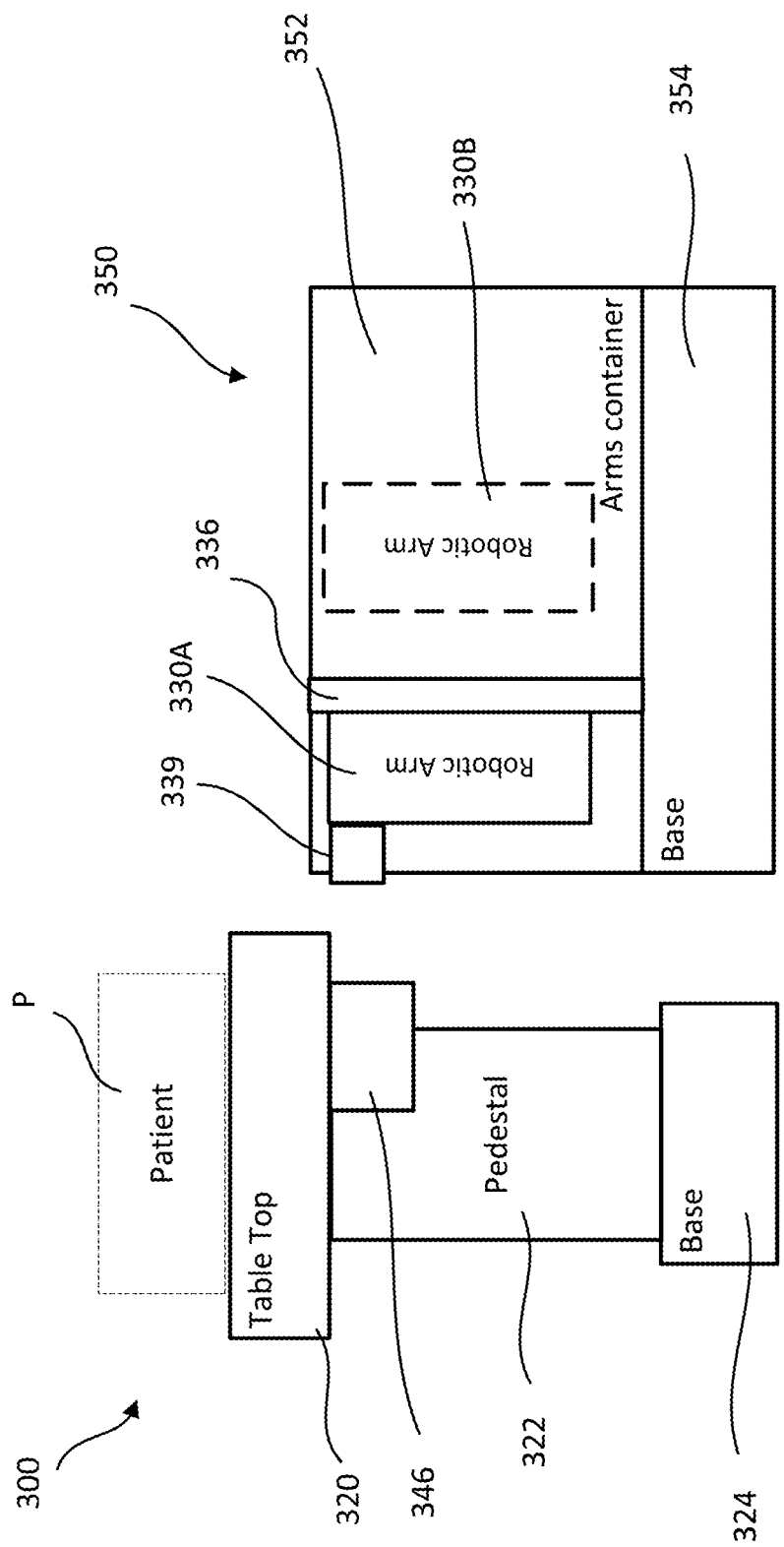
FIG. 3 is a schematic illustration of an arm cart and a surgical table, according to an embodiment.
Figure 4:
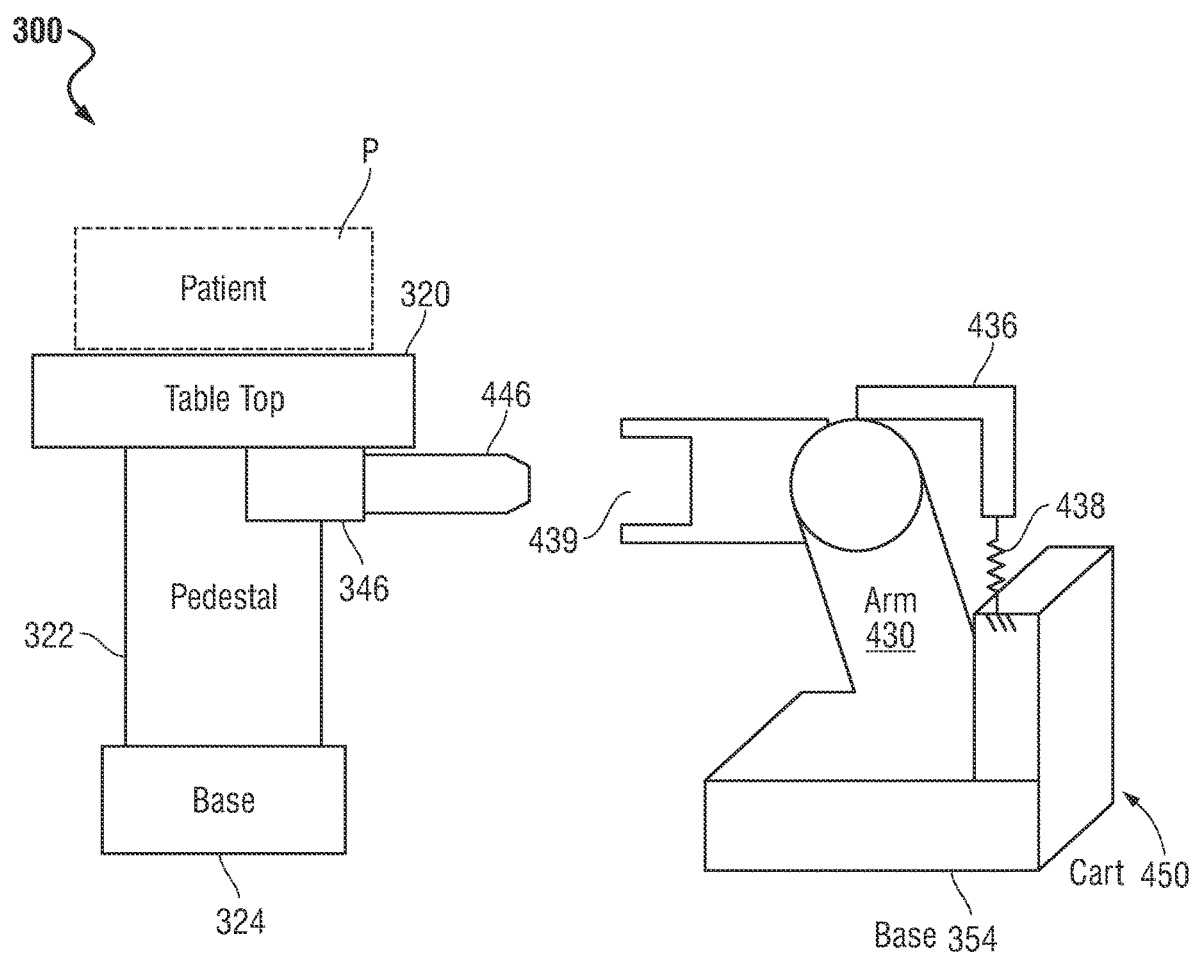
FIG. 4 is a schematic illustration of mating portions of a surgical table and a robotic arm, according to an embodiment.

FIG. 4 is a schematic illustration of mating portions of the surgical table 300 illustrated in FIG. 3 and a robotic arm 430, according to an embodiment. The coupling portion 346 of surgical table 300 includes a post 446 configured to be received by a socket 439 of the robotic arm 430. The robotic arm 430 is coupled to an arm cart 450 via a connector 436. The arm cart 450 may be the arm cart 350 shown in FIG. 3 and is depicted simplistically in FIG. 4 for ease of illustration. The connector 436 includes a spring 438 such that the connector 436 (and hence the robotic arm 430) can move relative to the arm cart 450. Similarly stated, a force applied to the robotic arm 430 and/or the connector 436 can cause the spring 438 to deform, allowing the robotic arm 430 to move. In this way, fine adjustments to position of the robotic arm 430 can be adjusted, for example to align the socket 439 to the post 446.

In some embodiments, the post 446 can be chamfered and/or beveled such that, when the post 446 contacts the socket 439, for example as the arm cart 450 is pushed towards the surgical table 400, if the post 446 and the socket 439 are not precisely aligned, the chamfer of the post 446 can apply a force to the socket 439 urging the socket 439 into closer alignment with the post 446. The spring 438 can deform in response to the force and the post 446 and the socket 439 can mate.

Figure 5:
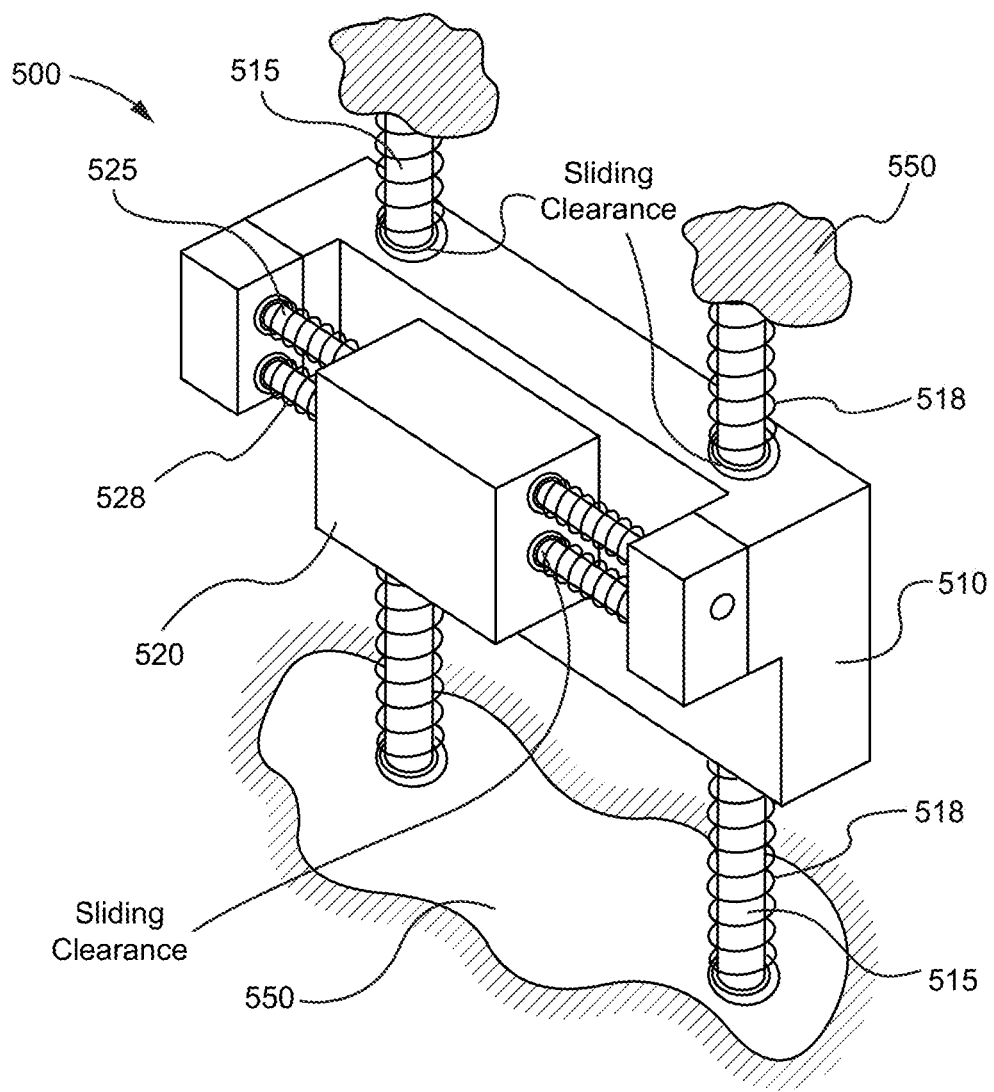
FIG. 5 is a schematic illustration of a connector of an arm cart, according to an embodiment.

FIG. 5 is a schematic illustration of a connector 500, according to an embodiment. The connector 500 can be structurally and/or functionally similar to the connectors 336 and/or 436 described above. The connector 500 can be operable to be connected to and/or support a robotic arm (not shown in FIG. 5) within an arm cart 550. The connector 500 can be operable to enable fine adjustments to the alignment of the robotic arm relative to the arm cart 550 and/or a surgical table (not shown in FIG. 5) to be made such that the robotic arm can be matingly coupled to the surgical table. As shown in FIG. 5 and described in further detail below, the connector 500 can provide two degrees of freedom, enabling the robotic arm to move in a horizontal and a vertical direction relative to the arm cart 550. For movement in the third dimension, the arm cart 550 itself can be moved towards and/or away from the surgical table.

The connector 500 includes two orthogonal prismatic (or sliding) joints. A first block 510 is operable to slide vertically on two vertical posts 515, each of which is fixedly coupled to the arm cart 550. Similarly stated, the first block 510 can define a through hole corresponding to each vertical post 515. The through hole and the vertical posts 515 can be sized such that a sliding clearance is defined. Although two vertical posts 515 are shown, any suitable number of vertical posts 515 can be used. It should be noted, however, that in some embodiments the presence of at least two vertical posts 515 and/or non-circular posts to constrain the first block 510 from rotating about the vertical axis can be desirable. Springs 518 are disposed over the vertical posts 515, although in other embodiments, springs 518 can be coupled to the arm cart 550 and the first block 510 in any suitable location (e.g., not necessarily coaxial with the posts 515). As shown, each vertical post 515 has two springs 518, one above and one below the first block 510, upper springs can resist movement of the first block 510 in one vertical direction, while the lower springs can resist movement of the first block 510 in the opposite vertical direction. In other embodiments, springs resisting movement of the first block 510 in the upward direction can be omitted, and the weight of the connector 500 and/or robotic arm against springs resisting movement of the first block 510 in the downward direction can maintain the first block 510 in a rest position.

A second block 520 is operable to slide horizontally on two horizontal posts 525, each of which coupled to the first block 510. In this way, the second block 520 has two degrees of freedom relative to the arm cart 550. Again, in some embodiments, the presence of at least two horizontal posts 525 and/or non-circular horizontal posts can be desirable to constrain the second block 520 from rotating about the axis of the horizontal posts 525. Thus, the second block 520 can be operable to move horizontally and vertically relative to the arm cart 550 while being constrained from any rotational movement. Springs 528 are disposed over the horizontal posts 525, although in other embodiments, springs 528 can be coupled to the first block 510 and the second block 520 in any suitable location (e.g., not necessarily coaxial with the posts 525). As shown, each horizontal post has two springs 528, one on either side of the second block 520. The opposing springs can be operable to resist movement of the second block 520 in opposite directions.

The second block 520 can include a latch, magnet, or other suitable coupling mechanism operable to be removeably coupled to the robotic arm. Thus, the robotic arm can be removeably coupled to the second block 520, and the connector 500 can allow the robotic arm to move with two degrees of freedom relative to the arm cart 550. The springs 518 and 528 can be operable to maintain the robotic arm in a rest position, but allow for limited movement (e.g., up to 2 cm in a vertical direction and up to 2 cm in a lateral direction, up to 10 cm in any direction, and/or any other suitable amount of movement) for fine adjustments of position and/or alignment while urging the robotic arm back to the rest position. The springs 518 and 528 have the added benefit of acting as shock absorbers cushioning the robotic arm during transit and/or impacts involving the arm cart 550. In some embodiments, stops can be coupled to the vertical posts 515 and/or the horizontal posts 525 such that motion of the first block 510 and/or the second block 520 can be limited by the stops.

Figure 6:
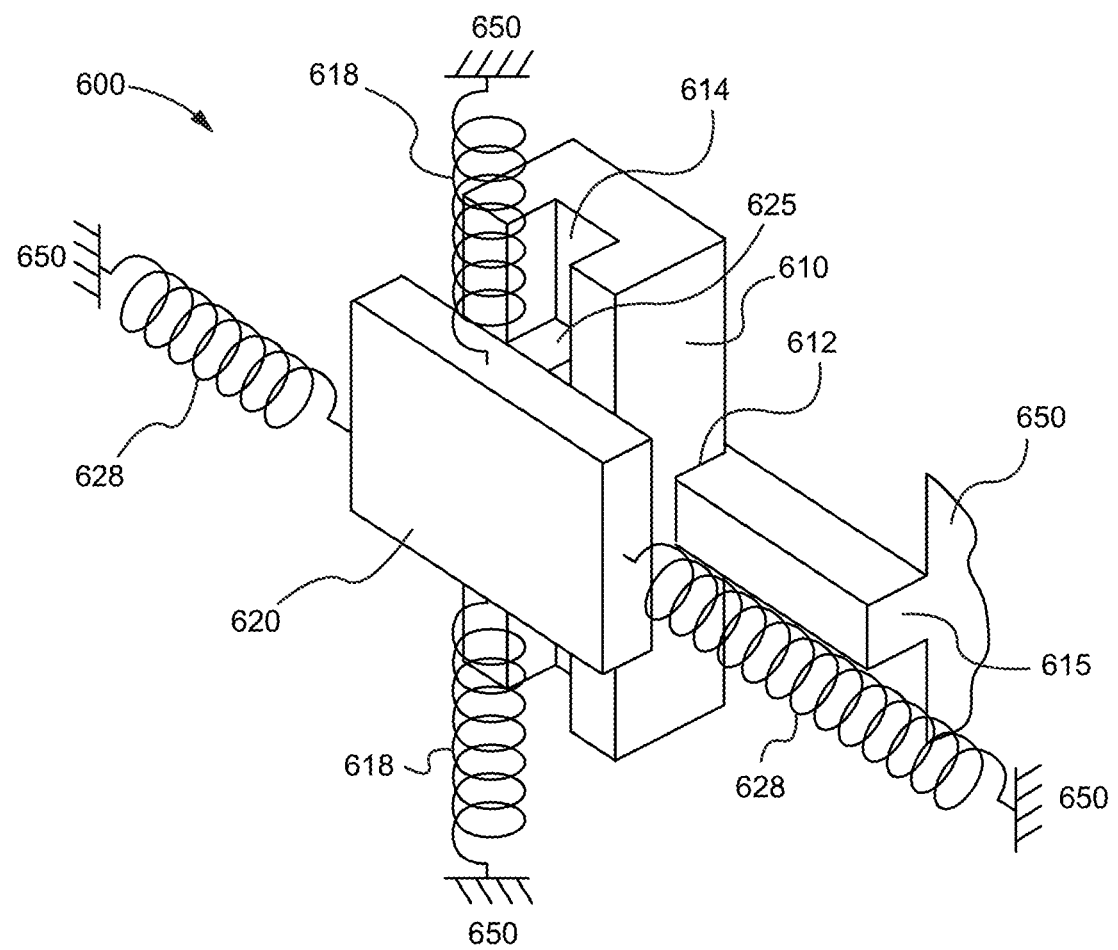
FIG. 6 is a schematic illustration of a connector of an arm cart, according to an embodiment.

FIG. 6 is a schematic illustration of a connector 600, according to an embodiment. The connector 600 is similar to the connector 500 described above and/or can be structurally and/or functionally similar to the connectors 336 and/or 436. The connector 600 includes a first block 610 and a second block 620 that are slideably coupled to each other such that the connector 600 has two degrees of freedom. The first block 610 includes a first groove 612 slideably coupled to a rail 615 of the arm cart. The second block 620 includes a tongue 625 slideably disposed within a second groove 614 of the first block 610. The second block 620 is configured to be coupled to a robotic arm. The connector 600 can be operable to be coupled to and/or support a robotic arm via the second block 620. Thus, the robotic arm and the second block 620 can move relative to the arm cart 650, which can permit fine adjustments as discussed above.

A first (e.g., vertical) set of opposed springs 618 and a second (e.g., lateral) set of opposed springs 628 are coupled to the second block 620 and the arm cart 650. The springs 618 and 628 can maintain the second block 620 and/or the robotic arm in a rest position while allowing for limited movement.

Figure 7:
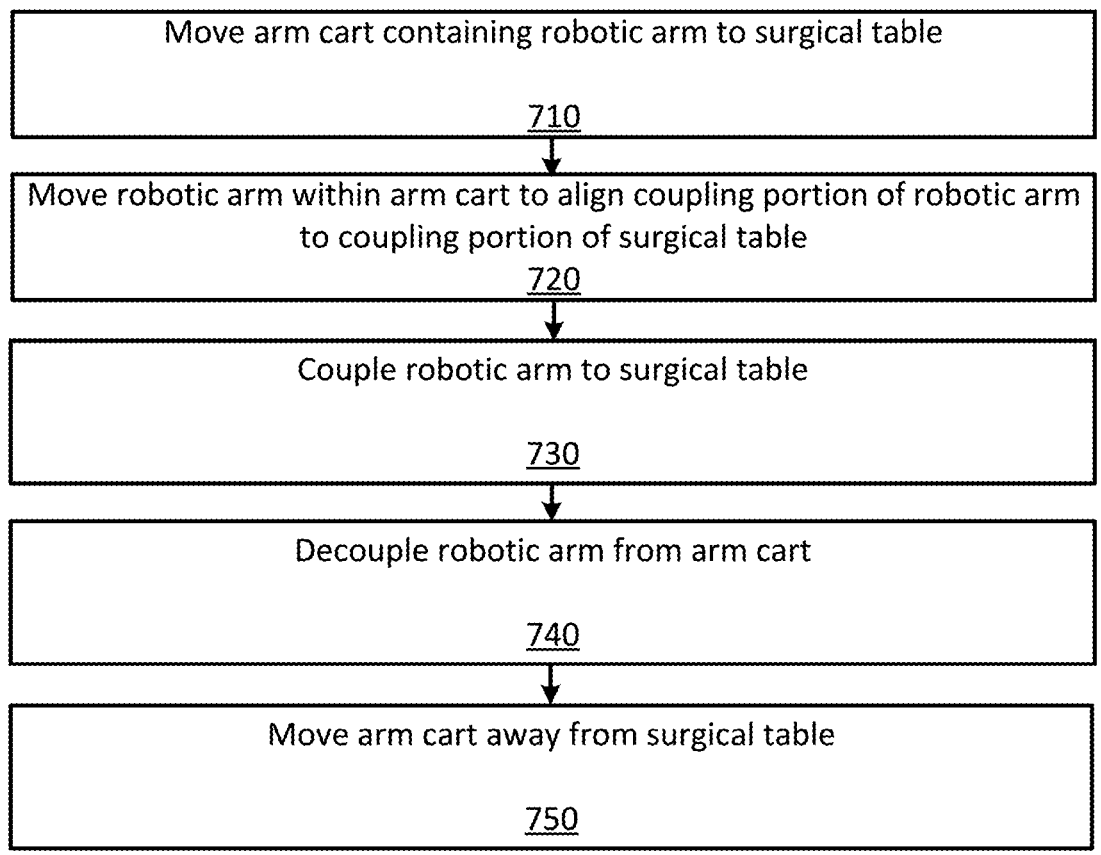
FIG. 7 is a flow chart of a method for coupling a robotic arm to a surgical table, according to an embodiment.

FIG. 7 is flow chart of a method of coupling a robotic arm to a surgical table, according to an embodiment. At 710, an arm cart containing a robotic arm can be moved to a surgical table, for example, from a storage location. Each of the robotic arm and arm cart can be similar to those described above. Moving the arm cart to the surgical table, at 710 can include orienting a coupling portion of the surgical arm adjacent to a corresponding coupling portion of the surgical table. For example, the arm cart can be placed near the surgical table (e.g., within a foot or less) such that the coupling portion of the surgical arm is approximately aligned with the corresponding coupling portion of the surgical table. For example, the arm cart can be positioned relative to the surgical table such that the coupling portion of the robotic arm is aligned (e.g., vertically and/or laterally) within less than 2 cm of the coupling portion of the surgical table. Similarly stated, when the arm cart is moved adjacent to the surgical table, the robotic arm can be in a first position in which springs (e.g., as shown in FIGS. 4-6) and the force of gravity on the connector and surgical arm are balanced. In the first position, the robotic arm may not be precisely aligned with the surgical table.

At 720, fine adjustments of the position of robotic arm within the arm cart can be made, for example, by applying a force to the robotic arm and/or the coupler, the robotic arm can move vertically and/or laterally (horizontally) relative to the arm cart. For example springs (as shown in FIGS. 4-6) can deform, but allow the robotic arm and coupler to move a sufficient distance to allow fine position adjustments (e.g., adjustments of 1.5-2 cm or any other suitable adjustments) to be made. In some embodiments, the coupler can be configured to allow the robotic arm (and the coupling portion of the robotic arm) to translate vertically and/or laterally, while constraining rotational movement. Constraining rotational movement, using, for example, tongue-and-groove prismatic joints (as shown, for example, in FIG. 6) and/or two or more rods (as shown, for example, in FIG. 5) can reduce or eliminate radial misalignment.

In some embodiments fine adjustment of the position of the robotic arm, at 720, can include pushing the arm cart towards the surgical table such that the coupling portion of the robotic arm contacts the coupling portion of the surgical table. As shown, for example, in FIG. 4, the coupling portion of the surgical table can include a chamfer or similar structure configured to apply a force to the coupling portion of the coupling portion of the arm cart. In this way, as the arm cart moves towards the surgical table, the movement of the arm cart can cause the coupling portions of the surgical table and arm cart to move into exact alignment. Exact alignment, as used in the present application, refers to the coupling portions of the robotic arm and the surgical table having relative positions such that the robotic arm can mate with the surgical table.

Once aligned, the robotic arm can be coupled to the surgical table, at 730. Then, the robotic arm can be decoupled from the connector and arm cart, at 740. Subsequently, the arm cart can be moved away from the surgical table, for example, to a storage location, at 750, and the arm can be prepared for use in a surgical procedure.

While various embodiments have been described above, it should be understood that they have been presented by way of example only, and not limitation. For example, with reference to FIG. 4, the coupling portion of the surgical table is shown and described as a post, while the coupling portion of the robotic arm is shown and described as a socket. It should be understood that in other embodiments, the coupling portion of the robotic arm can be a post and the coupling portion of the surgical table can be a socket.

As another example, in some embodiments, the coupling portions of the robotic arm and the surgical table can be directional, such as corresponding cruciform, star-shaped, or any other suitable coupling portions. In such an embodiment, constraining rotational movement of the robotic arm (e.g., using non-circular and/or multiple prismatic joints) can play an additional role in maintaining alignment of the coupling portions of robotic arm and the surgical table. As another example, although some embodiments describe the use of prismatic joints to permit fine adjustment of the robotic arm relative to the arm cart, any other suitable mechanism can be used. For example, rather than nested prismatic joints, two ball joints separated by a link can permit fine adjustment of the robotic arm with two degrees of freedom. As yet another example, although some embodiments describe vertical or horizontal (or lateral) structures (e.g. springs, rods, grooves, etc.) it should be understood that in other embodiments, springs, joints and the like can be in any orientation. For example, in some embodiments, rather than being oriented at 0 and 90 degrees, prismatic joints and/or springs can be oriented at 45 and 135 degrees.

As yet another example, some embodiments are described herein as containing springs. Springs can be operable to urge a connector and/or a robotic arm towards a rest position, while allowing fine adjustments of the connector and/or robotic arm. It should be understood, however, that in other embodiments, springs may be omitted and the connector and/or robotic arm can be movable relative to the arm cart, but may not include springs to urge the connector and/or robotic arm towards a rest position. Furthermore, where springs are described, it should be understood that any suitable mechanism operable to allow the connector to move and/or exert a force to urge the connector and/or robotic arm towards a rest position, such as a mechanical spring (e.g., coil spring, leaf spring, compression spring, extension spring, etc.), gas springs, hydraulic springs, magnets, linear actuators, etc. can be used. Some embodiments can also include dampers in parallel with or in series with springs.

Where methods described above indicate certain events occurring in certain order, the ordering of certain events may be modified. Additionally, certain of the events may be performed concurrently in a parallel process when possible, as well as performed sequentially as described above.

Where schematics and/or embodiments described above indicate certain components arranged in certain orientations or positions, the arrangement of components may be modified. While the embodiments have been particularly shown and described, it will be understood that various changes in form and details may be made. Any portion of the apparatus and/or methods described herein may be combined in any combination, except mutually exclusive combinations. The embodiments described herein can include various combinations and/or sub-combinations of the functions, components and/or features of the different embodiments described.

What is claimed is:

1. A surgical robotic system comprising:
a first robotic arm;
an arm cart configured to transport the first robotic arm between a surgical table and a storage location; and
a connector having a connector block, wherein the connector block is i) connected to the first robotic arm, and ii) biased against the arm cart by a spring, the connector block being slideably mounted to the arm cart such that the connector block and the first robotic arm can collectively move relative to the arm cart in two degrees of freedom, and movement in a third dimension or degree of freedom is achieved by the arm cart itself being moved towards and away from the surgical table.

2. The system of claim 1 further comprising a second robotic arm, wherein the arm cart is configured to transport the second robotic arm simultaneously with the first robotic arm, between the surgical table and the storage location.

3. The system of claim 1, wherein the connector block is mounted to the arm cart such that angular movement of the connector block and the first robotic arm relative to the arm cart is impeded.

4. The system of claim 3, wherein a force applied to the first robotic arm causes the spring to deform and thereby change a position of the first robotic arm relative to the arm cart so that the first robotic arm becomes aligned with a coupling portion of the surgical table to which the robotic arm is being coupled.

5. The system of claim 1 wherein the connector comprises a latch, magnet, or other coupling mechanism operable to be removeably coupled to the first robotic arm.

6. The system of claim 1, further comprising:
a first plurality of springs, each spring from the first plurality of springs being substantially horizontal, having a first end portion coupled to the arm cart, and having a second end portion coupled to the connector;
a second plurality of springs, each spring from the second plurality of springs being substantially vertical, having a first end portion coupled to the arm cart, and having a second end portion coupled to the connector;
the first plurality of springs and the second plurality of springs each configured to provide elastic resistance to moving the connector relative to the arm cart.

7. The system of claim 1 wherein a force applied to the first robotic arm causes the spring to deform and thereby change a position of the first robotic arm relative to the arm cart so that the first robotic arm becomes aligned with a coupling portion of the surgical table to which the first robotic arm is being coupled.

8. The system of claim 1, wherein the first robotic arm is coupled to the arm cart solely via the connector.

9. The system of claim 8 further comprising a second robotic arm, wherein the arm cart is configured to transport the second robotic arm simultaneously with the first robotic arm.

10. The system of claim 1 wherein the connector comprises a latch, magnet, or other coupling mechanism operable to be removeably coupled to the first robotic arm.

11. The system of claim 10 wherein the spring deforms when the first robotic arm moves relative to the arm cart to act as a shock absorber cushioning the first robotic arm during transit or impacts involving the arm cart.

12. The system of claim 11 wherein the first robotic arm is coupled to the arm cart solely via the connector.

13. The system of claim 10 wherein a force applied to the first robotic arm causes the spring to deform and thereby change a position of the first robotic arm relative to the arm cart so that the first robotic arm becomes aligned with a coupling portion of the surgical table to which the first robotic arm is being coupled.

14. The system of claim 13 wherein the first robotic arm is coupled to the arm cart solely via the connector.

* * * * *